United States Patent [19]
Hsieh

[11] Patent Number: 4,820,924
[45] Date of Patent: Apr. 11, 1989

[54] SCINTILLATION CAMERA AND THREE DIMENSIONAL MULTIFOCAL COLLIMATOR USED THEREWITH

[75] Inventor: Jiang Hsieh, Elk Grove Village, Ill.

[73] Assignee: Siemens Gammasonics, Inc., Des Plaines, Ill.

[21] Appl. No.: 67,059

[22] Filed: Jun. 25, 1987

Related U.S. Application Data

[63] Continuation-in-part of Ser. No. 944,700, Dec. 19, 1986.

[51] Int. Cl.⁴ .................. G01T 1/166; G21K 1/02
[52] U.S. Cl. ..................... 250/363.10; 250/363.04; 250/505.1
[58] Field of Search .............. 250/365 SB, 363 SH, 250/505.1; 378/149

[56] References Cited

U.S. PATENT DOCUMENTS 4,670,657 6/1987 Hawman et al. ............. 250/505.1

Primary Examiner—Carolyn E. Fields
Attorney, Agent, or Firm—Mark H. Jay

[57] ABSTRACT

A collimator has a plurality of focal points in the transaxial direction and at least one focal point in the axial direction. The shortest focal lengths are located at the center of the collimator. The longest focal length is located at the periphery of the collimator. The focal length increases between the minimum focal length and the maximum focal length.

13 Claims, 4 Drawing Sheets

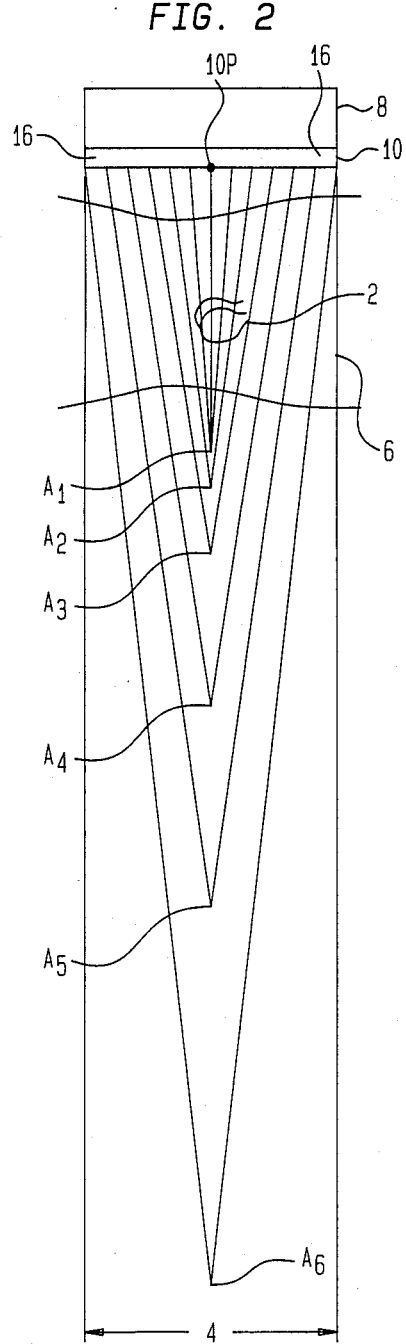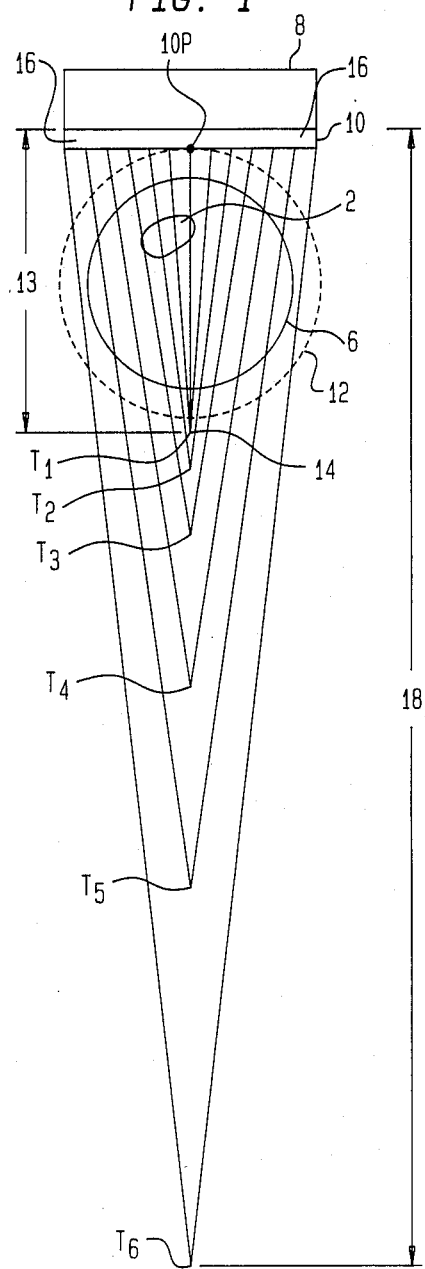

SCINTILLATION CAMERA AND THREE DIMENSIONAL MULTIFOCAL COLLIMATOR USED THEREWITH

CROSS REFERENCE TO RELATED APPLICATION

This application is a continuation-in-part of pending commonly-owned patent application Ser. No. 944,700 filed Dec. 19, 1986. The entire disclosure of this parent application, including the drawings thereof, is hereby incorporated into this application as if fully set forth herein.

BACKGROUND OF THE INVENTION

In the above-referenced parent patent application, there is disclosed a fan-beam collimator which has a plurality of focal lengths and which is therefore entitled a "multifocal collimator". The collimator there disclosed is a parallel beam collimator as viewed along the axial direction and has its plurality of focal lengths in the transaxial direction. Persons skilled in the art will understand that the term "axial direction" refers to a direction which is parallel to the axis of rotation of the collimator in rotational camera transaxial SPECT (single photon emission computed tomography). "Transaxial direction" means a view taken perpendicular this axis of rotation.

While the collimator described in the above-referenced parent patent application is highly advantageous as compared with known collimators, it would be desirable to further improve upon it while still preserving the improved center sensitivity and the lack of truncation errors and corresponding artifacts.

It is therefore one object of the invention to provide a multifocal collimator which improves upon the above-referenced multifocal fan-beam collimator.

Another object is to provide a scintillation camera system which will improve images of comparatively small body organs, such as the heart.

Another object of the invention is, in general, to improve upon known rotational camera transaxial SPECT scintillation camera systems.

SUMMARY OF THE INVENTION

In accordance with the invention, there is provided a scintillation camera system which uses a novel three-dimensional multifocal collimator. As viewed along the transaxial direction, the collimator appears identical to the collimator disclosed in the above-referenced parent application. However, in the axial direction, the collimator is a focusing collimator (and not a nonfocusing, parallel-hole collimator). In preferred embodiments, the invention has exactly one, or a plurality, of focal points in the axial direction. The focal lengths of the collimator are at a minimum in the center and at a maximum around the periphery.

The invention provides a further gain in sensitivity because it is a focusing collimator in both the transaxial and axial directions, rather than focusing in the transaxial direction alone. This permits a still better image to be produced in the same period of time, or alternatively permits an equally good image to be produced still faster.

BRIEF DESCRIPTION OF THE DRAWINGS

Exemplary and non-limiting preferred embodiments of the invention are shown in the drawings, in which:

FIG. 1 is a schematic transaxial view of a first preferred embodiment of the invention;

FIG. 2 is a schematic axial view of the first preferred embodiment;

DETAILED DESCRIPTION OF PREFERRED EMBODIMENTS

Figure 3:
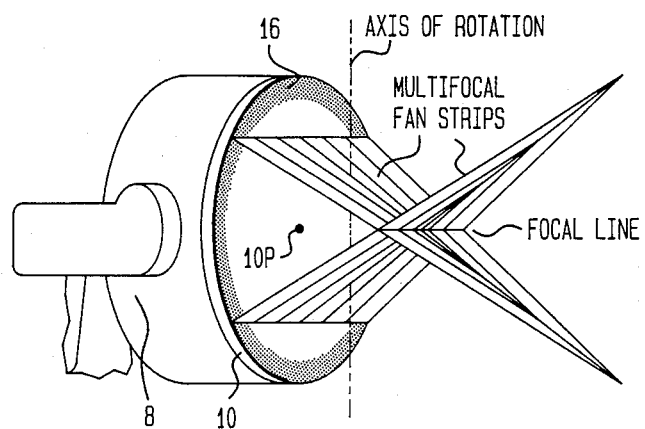
FIG. 3 is a schematic perspective view of the first preferred embodiment, showing a part of the gantry by which the camera head 8 is supported for use in rotational camera SPECT.

In the following description, it will be assumed that the invention will be used to image a patient's heart. However, it will be understood that this need not be the case and that any other organ can be imaged instead.

To image a patient's heart 2 it is necessary to image a slice 4 of the chest of a patient who is generally indicated by reference numeral 6. This slice 4 is approximately 17 cm in radius. To image this slice 4, a conventional scintillation camera head 8 and attached collimator 10 are rotated along a scan path 12 which is 20 cm in radius.

In a first preferred embodiment of the invention, the collimator 10 has a plurality of focal points as viewed transaxially ($T_1$, $T_2$ ... etc. in FIG. 1) and axially ($A_1$, $A_2$ ... etc. in FIG. 2). In each of the transaxial and axial cases, the focal length of the collimator is at a minimum adjacent the centerpoint 10P of the collimator 10 and at a maximum adjacent the peripheral region 16. The minimum focal length 13 is 45 cm, i.e. long enough to place the focal point 14 just outside the patient 6. The maximum focal length 18 is 130 cm, i.e. long enough so that no part of the slice 4 is truncated because the view of the collimator 10 is slightly wider than the width of the patient 6.

In the first preferred embodiment, the variation of focal length is the same in both the axial and transaxial cases. This is merely for convenience and is not a part of the invention; the focal length variation is the axial view may differ from the focal length variation in the transaxial view. Further, the minimum focal length in the axial case need not be the same as in the transaxial case, and likewise for the maximum focal length.

In the first preferred embodiment, the collimator 10 has a focal length which various continuously with distance; advantageously, the focal length f is determined by the equation:

$$f(x) = R + \cfrac{R}{\left(\cfrac{f_{min}}{f_{min} - R}\right)\left(\cfrac{w-x}{w}\right)^2 - \left(\cfrac{f_{max}}{f_{max} - R}\right)\left(\cfrac{x}{w}\right)^2}$$

where

R = radius of rotation
$f_{min}$ = 45 cm (short focal length)

$f_{max} = 130$ cm (long focal length)
w = half width of the collimator
x = distance of the point from center of the collimator either in transaxial or axial direction It will be understood that FIGS. 1 and 2 are exaggerated for clarity and that there are actually hundreds of closely spaced focal points rather than the few points which are shown spaced widely apart.

Figure 4:
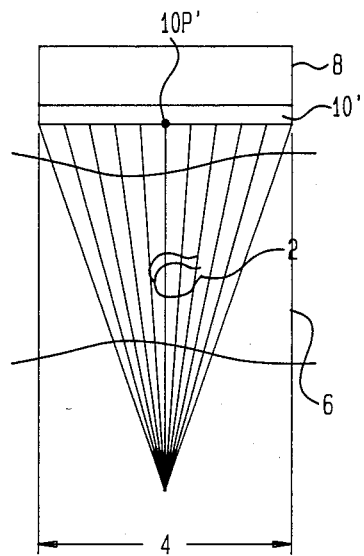
FIG. 4 is a schematic axial view of a second preferred embodiment.

Alternatively, there may be only one focal point in the axial direction; this is illustrated in FIG. 4.

The first preferred embodiment has a volume sensitivity gain of 2.5 when used for imaging the heart, as compared with the sensitivity of parallel collimators of comparable resolution.

Because the focal length of the collimator varies, the magnification of the image varies as a function of position. To take this into account, the geometrical relationships illustrated in FIG. 5 may be utilized.

Figure 5:
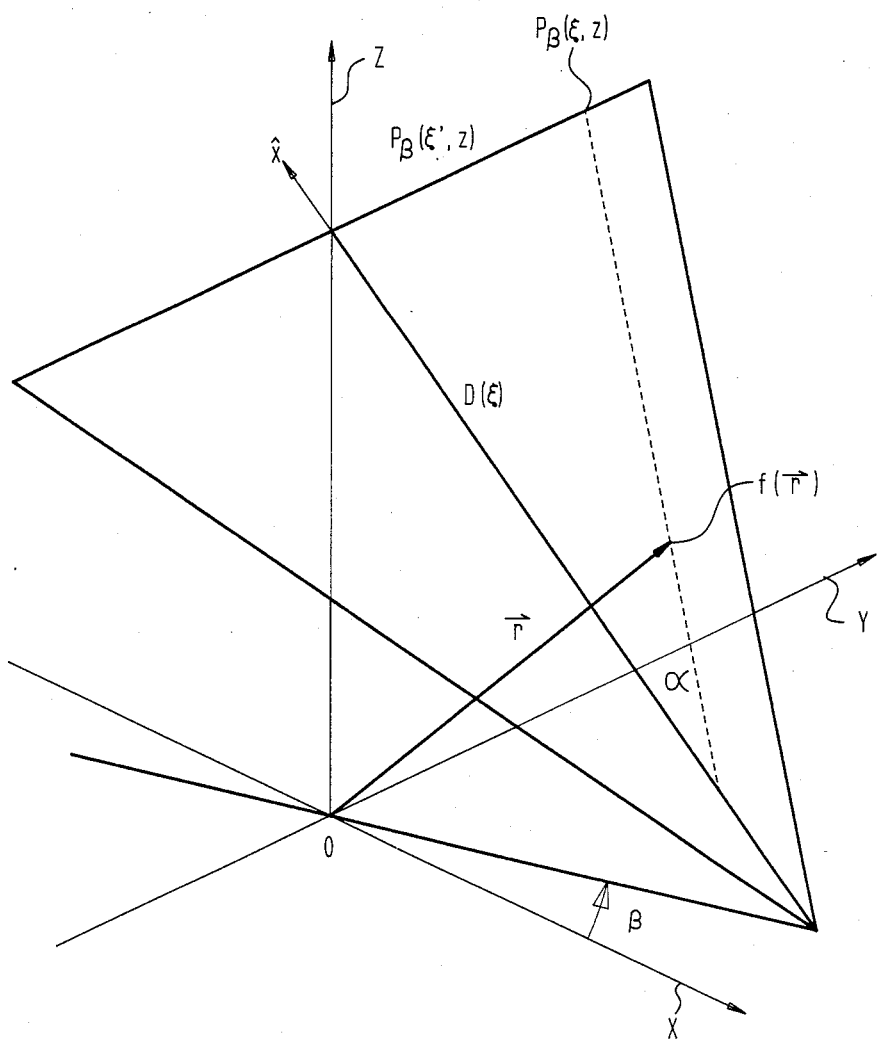
FIG. 5 is a diagram illustrating the geometry of the preferred embodiment.

In FIG. 5, $f(\vec{r})$ represents the point to be reconstructed and $P_\beta(\epsilon,z)$ represents the projection image acquired during a single view. A representation of is given by $$f(\vec{r}) = \frac{1}{4\pi^2} \oint g_\beta''(\iota,\epsilon) \frac{D^2(\iota)}{[D(\iota) + \vec{r}\cdot\vec{x}]^2} d\beta$$

where $g''_\beta(\epsilon,z)$ is the filtered and normalized image acquired during the view under consideration and is given by $$g_\beta''(\iota,\epsilon) = \int_{-\infty}^{\infty} d\epsilon' \int_{-\infty}^{\infty} d\iota' g_\iota\left(\iota - \frac{\sigma}{\sigma'}\iota'\right) g_\epsilon(\epsilon - \epsilon') \cdot J \cdot P_\beta(\iota',\epsilon)$$

where $$\sigma = \frac{D(o)}{D(o) + \vec{r}\cdot\vec{x}} \; ; \; \sigma' = \frac{D(\iota')}{D(\iota') + \vec{r}\cdot\vec{x}}$$

$$J = \frac{\partial D'(\iota)}{\partial \iota'} \sin\alpha' + \frac{\partial \alpha'}{\partial \iota'} D'\cos\alpha'$$

and $$g_\iota(\iota) = R_e \int_o^{w_{30}} wdw \exp(iw\iota)$$

$$g_\epsilon(\epsilon) = \frac{\sin w_{\epsilon o}\epsilon}{\pi\epsilon}$$

Figure 6:
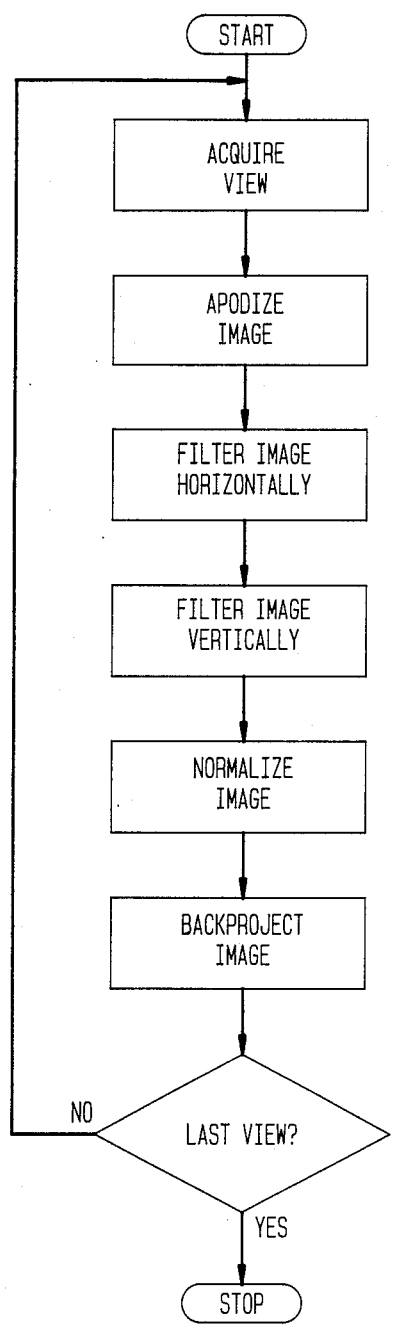
FIG. 6 is a flowchart of a preferred method of using the invention.

If it is assumed that the convolution filter can be approximated as spatially invariant, computation speed can be increased, and the image reconstruction can follow the flowchart shown in FIG. 6.

First, the individual view is acquired. Next, the image is apodized. Thereafter, the apodized image is filtered, first horizontally, and next vertically, although the order is not part of the invention and vertical filtering can precede horizontal filtering. The apodized and filtered view is normalized to correct for the different magnifications caused by the different focal lengths of the collimator. Finally, the apodized, filtered, and normalized image is backprojected into the image space and added to whatever previously processed data is present there. This process is repeated for each view until all views have been acquired.

Those skilled in the art will understand that changes can be made in the preferred embodiments here described, and that these embodiments can be used for other purposes. Such changes and uses are within the scope of the invention, which is limited only by the claims which follow.

What is claimed is:

1. A rotational camera transaxial SPECT collimator having a plurality of focal points as viewed along a first direction and at least one focal point as viewed along a second direction which is perpendicular to said first direction.

2. The collimator of claim 1, wherein said first direction is a transaxial direction and wherein said second direction is an axial direction.

3. The collimator of claim 2, wherein there is exactly one focal point as viewed along said axial direction.

4. The collimator of claim 3, wherein said one focal point is at most 130 centimeters distant from a rear face of the collimator.

5. The collimator of claim 1, wherein the collimator has a plurality of focal points as viewed axially and as viewed transaxially.

6. The collimator of claim 5, wherein, as viewed axially and as viewed transaxially, the closest focal point is 45 centimeters distant from a rear face of the collimator and the most remote focal point is 130 centimeters distant from said rear face.

7. A rotational camera transaxial SPECT collimator having a plurality of focal lengths as viewed along an axial direction and as viewed along a transaxial direction, and in which, for focal lengths in each of said axial and transaxial directions,
   a minimum focal length exists adjacent a centerpoint of the collimator,
   a maximum focal length exists adjacent a periphery of the collimator, and
   the focal length of the collimator is nondecreasing from said minimum focal length to said maximum focal length as distance from said centerpoint increases.

8. The collimator of claim 7, wherein said minimum focal length is approximately 45 centimeters and said maximum focal length is approximately 130 centimeters.

9. A rotational camera transaxial SPECT collimator having a single focal length as viewed along an axial direction and a plurality of focal lengths as viewed along a transaxial direction and in which, has focal lengths in said transaxial direction,
   a minimum focal length exists adjacent a centerpoint of the collimator,
   a maximum focal length exists adjacent a periphery of the collimator, and
   the focal length of the collimator is nondecreasing from said minimum focal length to said maximum focal length as distance from said centerpoint increases.

10. The collimator of claim 9, wherein said minimum focal length is approximately 45 centimeters and said maximum focal length is approximately 130 centimeters.

11. A rotational camera transaxial SPECT scintillation camera system, comprising:
   a scintillation camera head;
   a gantry supporting the scintillation camera head for use in rotational camera transaxial SPECT; and
   a collimator having a plurality of focal points as viewed along a first direction and at least one focal point as viewed along a second direction which is perpendicular to said first direction.

12. The system of claim 11, wherein said first direction is a transaxial direction, said second direction is an axial direction, and wherein there is exactly one focal point as viewed from said axial direction.

13. The system of claim 11, wherein said first direction is a transaxial direction, said second direction is an axial direction, and wherein there are a plurality of focal points as viewed from said axial direction.

* * * * *